(12) United States Patent
Mayer et al.

(10) Patent No.: US 10,303,210 B2
(45) Date of Patent: May 28, 2019

(54) ELECTRONIC DEVICES WITH WRIST STRAPS

(71) Applicant: Apple Inc., Cupertino, CA (US)

(72) Inventors: Kirk M. Mayer, San Francisco, CA (US); Yoji Hamada, Wakayama (JP); Liming Wang, Windham, NH (US)

(73) Assignee: Apple Inc., Cupertino, CA (US)

( * ) Notice: Subject to any disclaimer, the term of this patent is extended or adjusted under 35 U.S.C. 154(b) by 143 days.

(21) Appl. No.: 15/237,497

(22) Filed: Aug. 15, 2016

(65) Prior Publication Data

US 2018/0042368 A1    Feb. 15, 2018

(51) Int. Cl.
*A45F 5/00*       (2006.01)
*A61B 5/00*       (2006.01)
*G06F 1/16*       (2006.01)
*G04G 17/00*      (2013.01)

(52) U.S. Cl.
CPC ............... *G06F 1/163* (2013.01); *A45F 5/00* (2013.01); *A61B 5/681* (2013.01); *G04G 17/00* (2013.01); *A45F 2005/008* (2013.01); *A45F 2200/0508* (2013.01); *A45F 2200/0558* (2013.01)

(58) Field of Classification Search
CPC ............ G06F 1/163; A45F 5/00; A61B 5/681; G04G 17/00
See application file for complete search history.

(56) References Cited

U.S. PATENT DOCUMENTS

| | | | |
|---|---|---|---|
| 4,537,822 A | 8/1985 | Nanri et al. | |
| 5,508,098 A * | 4/1996 | Omar | B32B 5/26 442/319 |
| 5,823,012 A * | 10/1998 | Hacskaylo | A41D 20/00 66/171 |
| 6,307,751 B1 * | 10/2001 | Bodony | G06F 1/16 361/679.08 |
| 6,443,187 B1 * | 9/2002 | Wang | A44B 18/0023 139/391 |
| 6,546,603 B1 * | 4/2003 | Wang | A44B 18/0023 24/265 WS |
| 6,708,733 B2 | 3/2004 | Iizuka | |
| 9,677,207 B2 * | 6/2017 | Hurd | A41B 17/00 |
| 9,720,443 B2 * | 8/2017 | Malhotra | G06F 1/163 |
| 2002/0077578 A1 * | 6/2002 | Bonutti | A61F 5/0104 602/75 |
| 2006/0117458 A1 * | 6/2006 | Ishihara | A41D 1/002 2/170 |

(Continued)

*Primary Examiner* — Nidhi Thaker
(74) *Attorney, Agent, or Firm* — Treyz Law Group, P.C.; G. Victor Treyz; Kendall W. Abbasi

(57) ABSTRACT

A portable electronic device may have an electronic device strap. The strap may include inner and outer fabric layers and optional intermediate fabric layers. The inner fabric layer may have strands of material that are characterized by a larger denier per filament value than the outer fabric layer to help draw moisture away from the body of a user. The fabric layers may have stretchable warp fibers that allow the strap to be stretched. Weft fibers at the bottom of grooves that span the width of the strap may be provided with different colors than other weft strands. When the strap is stretched, the visibility of the weft fibers at the bottoms of the grooves may increase. A hook-and-loop fastener may be used to close the strap. Loops for the fastener may be formed from warp strands and may have multiple sizes.

17 Claims, 8 Drawing Sheets

(56) References Cited

U.S. PATENT DOCUMENTS

| | | |
|---|---|---|
| 2009/0062892 A1 | 3/2009 | Ilcheva et al. |
| 2012/0178343 A1 | 7/2012 | Hurd et al. |
| 2013/0146659 A1* | 6/2013 | Zhou .................... G06Q 20/355 |
| | | 235/380 |
| 2015/0282531 A1 | 10/2015 | Mayer et al. |
| 2016/0136882 A1* | 5/2016 | Cobbett ............... A61B 5/0205 |
| | | 156/218 |

* cited by examiner

US 10,303,210 B2

ELECTRONIC DEVICES WITH WRIST STRAPS

BACKGROUND

This relates generally to electronic devices and, more particularly, to electronic devices with wrist straps.

Portable electronic devices such as wristwatches have wrist straps. Straps may be formed from materials such as metal, plastic, and fabric. When a user is involved in athletic activities, the user may perspire. Moist fabric may not feel comfortable next to a user's skin. There is therefore a risk that a fabric strap may become uncomfortable as perspiration from a user's wrist soaks into the strap.

SUMMARY

An electronic device may have a strap. The strap may be formed from multiple layers of fabric. The strap may include an inner fabric layer that rests on a body part of a user and an outer fabric layer that faces away from the body part of the user. The outer fabric layer may have strands of material that are characterized by a smaller denier per filament value than the inner fabric layer to help draw moisture away from the body part of the user due to capillary action.

The fabric layers may have stretchable warp fibers that allow the strap to be stretched. Weft fibers at the bottom of grooves that span the width of the strap may be provided with different colors than other weft strands. When the strap is stretched, the visibility of the weft fibers at the bottoms of the grooves may increase.

A hook-and-loop fastener may be used to close the strap. Hooks for the hook-and-loop fastener may be coupled to the inner fabric layer. Loops for the fastener may be formed from warp strands in the outer fabric layer. The warp strands may have portions that form loops of different sizes to enhance engagement with the hooks.

DETAILED DESCRIPTION

Electronic devices may be provided with straps. The straps may be formed from fabric. The fabric may be woven fabric or knit fabric or may be formed by intertwining strands of material using braiding techniques or other intertwining techniques. The electronic devices may be wristwatches, fitness bands, or other electronic devices. Illustrative configurations in which portable electronic devices such as wristwatch devices or other wrist-mounted portable electronic devices are provided with woven fabric straps may sometimes be described herein as an example. In general, any suitable portable electronic device may be provided with a strap and the strap may be formed from any suitable fabric material. The straps or other fabric structures may be used to attach the portable electronic device to an arm, leg, head, torso, wrist, or other portion of a user's body.

Figure 1:
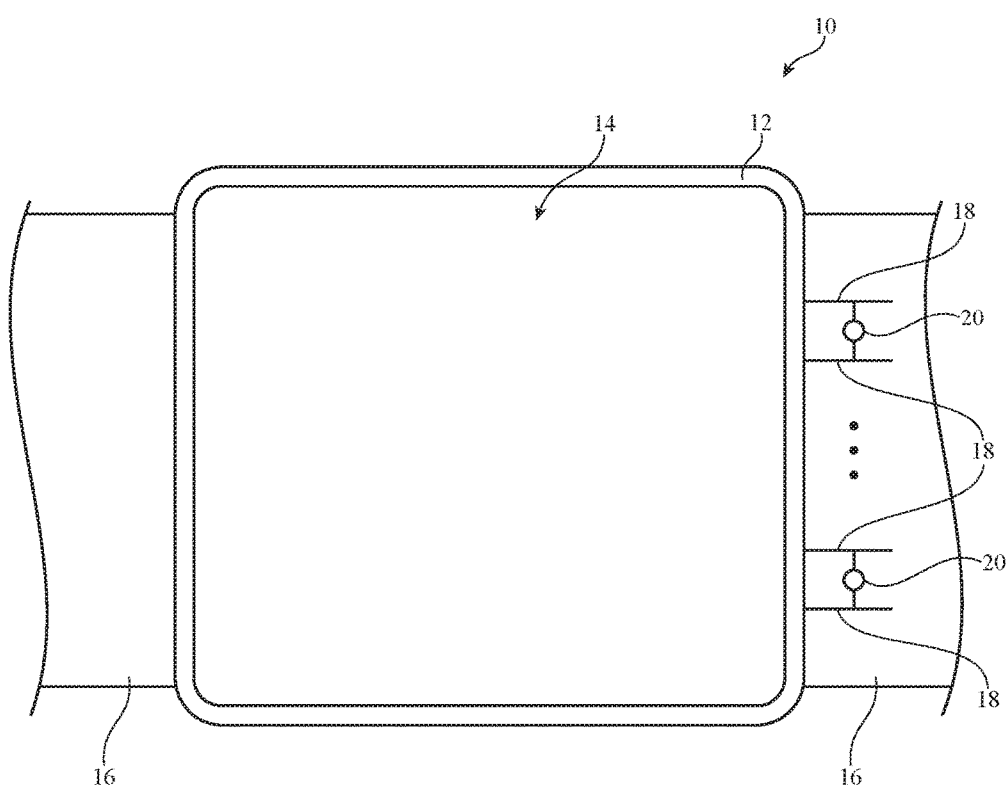
FIG. 1 is a top view of an illustrative electronic device with a fabric strap in accordance with an embodiment.

An illustrative electronic device is shown in FIG. 1. As shown in FIG. 1, device 10 may have a display such as display 14 and other electrical components mounted in a housing such as housing 12. Device 10 may be a portable electronic device such as a device that is mounted on a user's wrist, arm, leg, head, torso, or other body part. Device 10 may, for example, be a wrist-mounted device such as a wristwatch, a health monitoring device, a media player, a wireless key, or other electronic device and/or equipment that includes the functions of two or more of these devices or other suitable devices. Housing 12 (e.g., a watch housing in scenarios in which device 10 is a wristwatch) may be formed from metal, ceramic, plastic, glass, sapphire or other crystalline materials, and/or other suitable materials. Housing 12 may have a rectangular outline, may have an oval or circular shape, or may have other suitable shapes. Display 14 may be a liquid crystal display, an organic light-emitting diode display, or other suitable display.

Strap 16 may have portions attached to opposing sides of housing 12. Strap 16 may be coupled to pins or other structures that are attached to the exterior of housing 12 (as an example). A clasp formed from hook-and-loop fasteners or other suitable clasp may be used to secure strap 16 about the wrist or other body part of a user.

Strap 16 may include strands of material that are woven together. The strands of material that are woven to form strap 16 may be monofilaments and/or multifilament yarns. Strap 16 may contain insulating strands of material and/or conductive strands of material. Insulating strands may be formed from dielectric materials such as polymers. Conductive strands may be formed from metal wires or may be formed from one more conductive layers of material such as metal layers on polymer cores or other polymer layers. Conductive strands may also be formed by mixing conductive filaments with insulating filaments. Conductive strands may have insulating coatings.

If desired, strap 16 may contain electrical components such as components 20. Components 20 may include sensors, buttons, light-emitting diodes, batteries, antennas, integrated circuits, vibrators and other actuators, and/or other input-output devices. Conductive strands of material such as strands 18 may be used in routing power and data signals between components 20 within strap 16 and between components such as component 20 in strap 16 and circuitry in housing 12.

Figure 2:
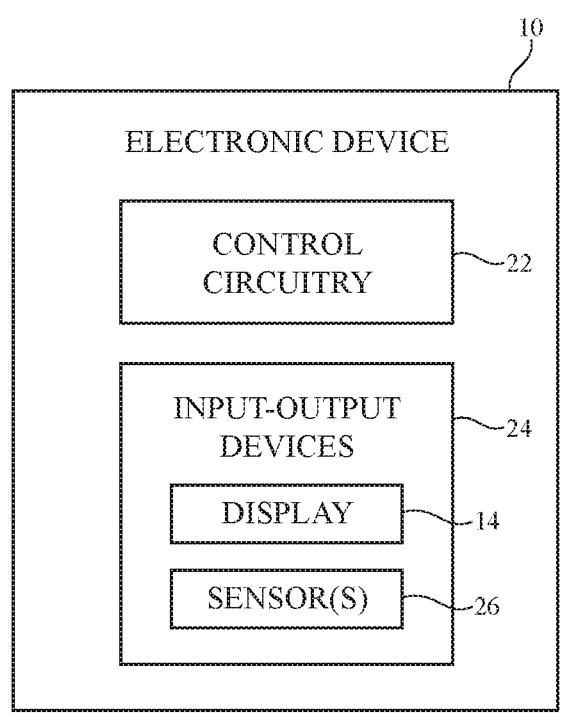
FIG. 2 is a schematic diagram of an illustrative electronic device in accordance with an embodiment.

A schematic diagram of an illustrative electronic device such as device 10 of FIG. 1 is shown in FIG. 2. As shown in FIG. 2, device 10 may include control circuitry 22. Control circuitry 22 may include processing circuitry such as microprocessors, digital signal processors, microcontrollers, baseband processors, image processors, application-specific integrated circuits with processing circuitry, and/or other processing circuitry and may include random-access memory, read-only memory, flash storage, hard disk storage, and/or other storage (e.g., a non-transitory storage media for storing computer instructions for software that runs on control circuitry 22).

Device 10 may include electrical components in housing 12 and/or in strap 16 that form input-output circuitry such as input-output devices 24. Input-output devices 24 may be used to allow data to be supplied to device 10 from external devices and from a user and to allow data to be provided from device 10 to external devices and the user. Input-output devices 24 may include buttons, joysticks, scrolling wheels, touch pads, key pads, keyboards, microphones, speakers, tone generators, vibrators, haptic devices, cameras, light-emitting diodes and other status indicators, displays such as display 14, data ports, etc. Sensors 26 of input-output devices 24 may include touch sensors, force sensors, accelerometers, compasses, magnetic sensors, gas sensors, pressure sensors, temperature sensors, capacitive proximity sensors, light-based proximity sensors, digital image sensors, ambient light sensors, heart rate sensors and blood oxygen sensors (e.g., sensors having a light emitter that emits light into a user's skin and the detects and processes reflected light), and other sensing circuits.

Device 10 may include wireless circuitry (e.g., wireless transceivers, antennas, etc.) for supporting wireless local area network communications, cellular telephone communications, near field communications, wireless power transmission and reception operations, and other wireless communications and power transfer operations.

Figure 3:
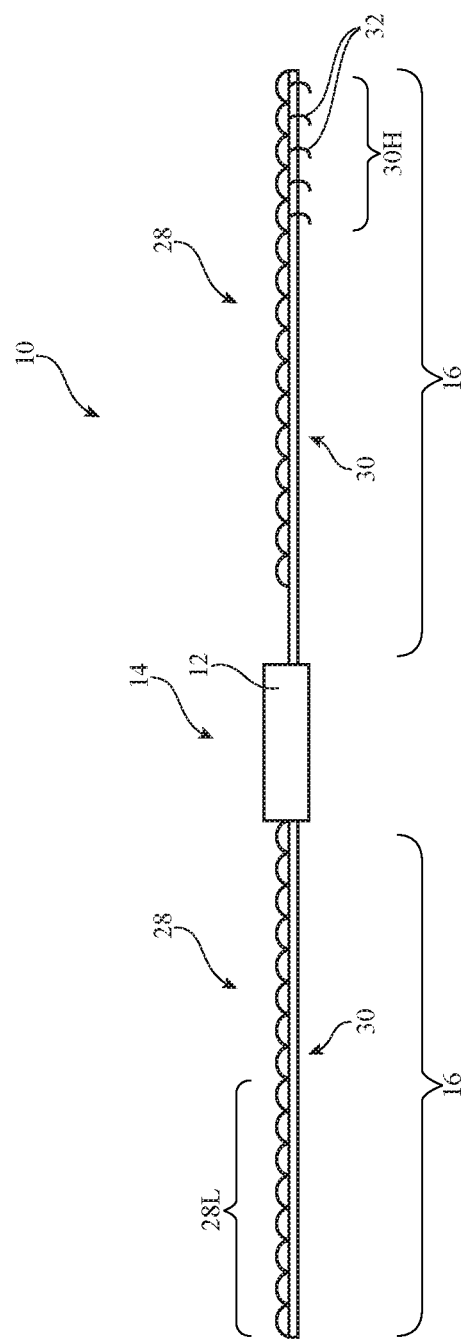
FIG. 3 is a cross-sectional side view of an illustrative electronic device with a wrist strap in accordance with an embodiment.

A cross-sectional side view of an illustrative device such as device 10 of FIG. 1 is shown in FIG. 3. As shown in FIG. 3, strap 16 may have an outer surface (front side) such as outer surface 28 and may have an opposing inner surface (rear side) such as inner surface 30. A clasp for strap 16 may be formed using magnets, interlocking prongs and holes, snaps, or other clasp mechanisms. With one illustrative configuration, which is shown in FIG. 3, strap 16 has a clasp formed from mating hook-and-loop fasteners. Portion 30H of inner surface 30 of strap 16 may have hooks 32 and at least portion 28L on the outer surface of strap 16 may have mating loops. If desired, most or all of outer surface 28 of strap 16 may have loops (e.g., so that outer surface 28 has a uniform appearance).

Figure 4:
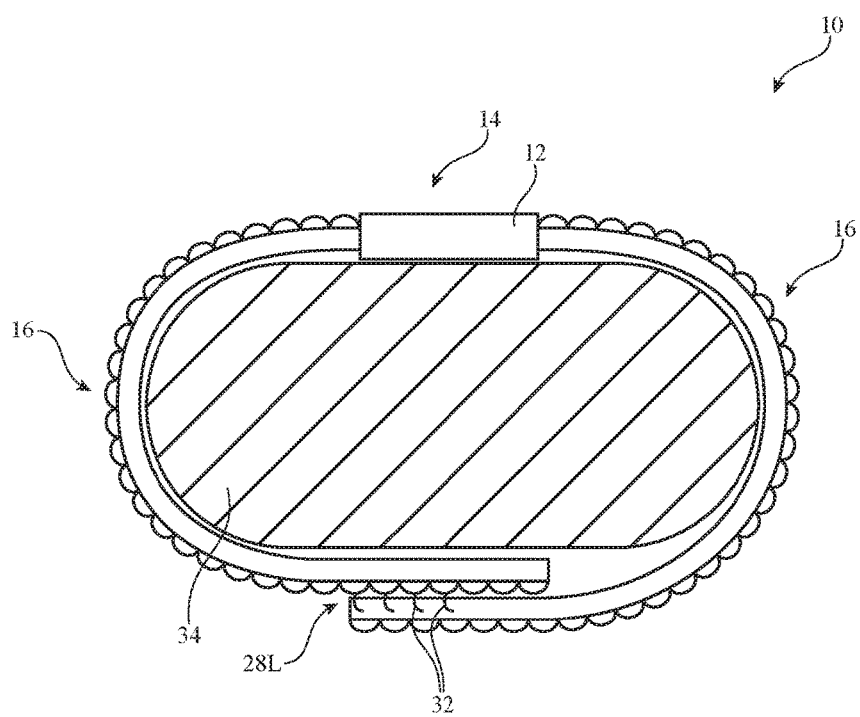
FIG. 4 is a cross-sectional side view of the illustrative electronic device of FIG. 3 in a configuration in which the wrist strap has been wrapped around a user's wrist in accordance with an embodiment.

As shown in FIG. 4, when strap 16 is wrapped around a user's wrist or other body part such as wrist 34, hooks 32 engage the loops of portion 28L and thereby close the hook-and-loop fastener formed from hooks 32 and the loops of portion 28L. When it is desired to open the clasp formed from the hook-and-loop fastener of strap 16, a user may pull outwardly on the end of strap 16 that is adjacent to hooks 32, thereby pulling hooks 32 away from the mating loops on portion 28L of strap 16.

The loops that are formed in region 28L of surface 28 may, if desired, be formed from portions of the strands of material that are woven to form strap 16 (i.e., the strands of material that are used in forming strap 16 may have portions that extend outwardly from the rest of the fabric forming strap 16 so that these loop portions may be engaged by hooks 32). Hooks 32 may be individually incorporated into strand 16 or may be mounted on a fabric strip or other support layer that is attached to strap 16 with adhesive, by sewing, by welding (e.g., laser welding), by intertwining the strands of material that form strap 16 with hooks 32, by crimping hooks 32 to strap 16, by molding hooks 32 to strap 16, or by using other suitable attachment mechanisms. Hooks 32 may be formed from metal, from plastic, from portions of the strands of material in fabric 16, or from other suitable materials.

Figure 5A:
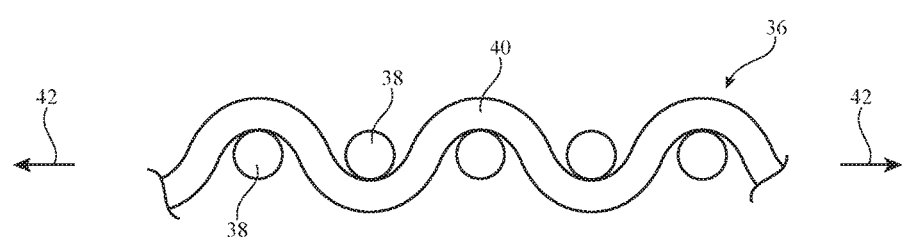
FIG. 5A is a cross-sectional side view of an illustrative fabric layer in a strap in an unstretched configuration in accordance with an embodiment.
Figure 5B:
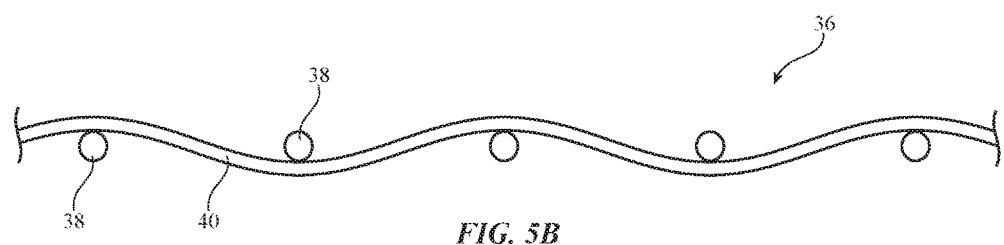
FIG. 5B is a cross-sectional side view of the fabric layer of FIG. 5A in a stretched configuration in accordance with an embodiment.

The fabric that forms strap 16 may have one or more stretchable layers. Consider, as an example, the illustrative fabric of FIG. 5A. Fabric 36 has weft strands 38 and warp strands 40. Warp strands 40 (and, if desired, some or all of weft strands 38) may be formed from stretchable material such as stretchable polyurethane. Due to the presence of stretchable warp strands 40, fabric 36 may stretch when pulled in directions 42, as illustrated in FIG. 5B. Stretchable strands such as warp strands 40 may be oriented to run around the user's wrist (i.e., the warp strands in straps 16 may be oriented so that they extend along the elongated longitudinal dimension of strap 16). This allows a user to stretch strap 16 tightly around wrist 34 or other body part (e.g., to ensure that a satisfactory heart rate monitor signal is picked up by a heart rate monitor in device 10, etc.). If desired, the fabric forming strap 16 may contain non-stretchable strands of material (e.g., polyester, etc.). Non-stretchable strands of material may, for example, be used to provide strap 16 with strength and/or moisture management capabilities.

Figure 6A:
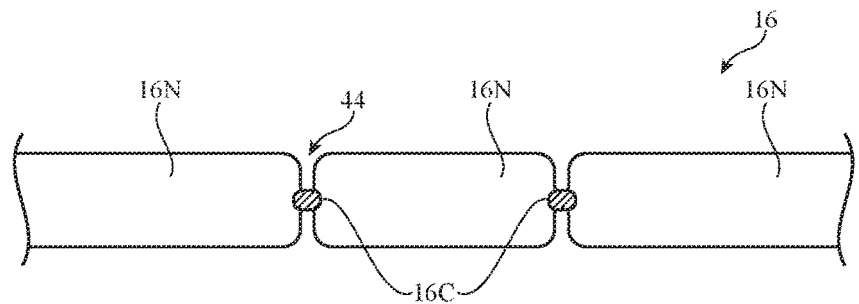
FIG. 6A is a cross-sectional side view of an illustrative fabric strap in an unstretched configuration in accordance with an embodiment.
Figure 6B:
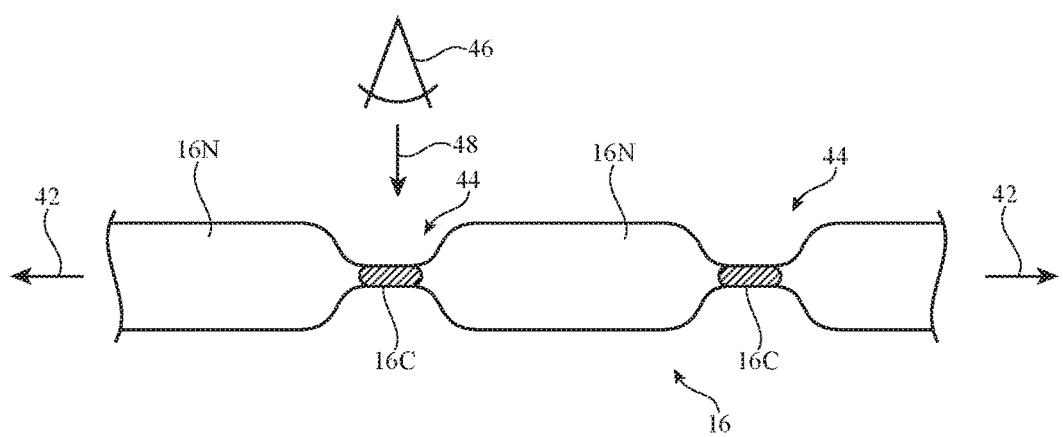
FIG. 6B is a cross-sectional side view of the fabric strap of FIG. 6A in a stretched configuration in accordance with an embodiment.

FIG. 6A is a cross-sectional side view of strap 16 showing how strap 16 may have grooves 44 (sometimes referred to as valleys) that extend across the width of strap 16 (i.e., into the page in the orientation of FIG. 6A) at periodic locations along the length of strap 16. Strap 16 may be formed from strands of different colors. For example, strands of material at the bottom of each groove 44 such as strands 16C (e.g., weft strands) may have a different color than strands 16N at other portions of strap 16. When strap 16 is not stretched, strands 16C are fully or partly obscured by the narrow shape of grooves 44. When strap 16 is stretched in directions 42 as shown in FIG. 6B, grooves 44 widen so that the visibility of colored strands 16C increases. As a result, a user such as user 46 who is viewing strap 16 in direction 48 can readily see colored strands 16C and can thereby be informed that strap 16 is in its stretched configuration. The use of visual feedback of this type may help a user adjust strap 16 to a desired tightness level to support accurate heart rate monitoring or other sensor functions performed by the electrical components of device 10.

Figure 7:
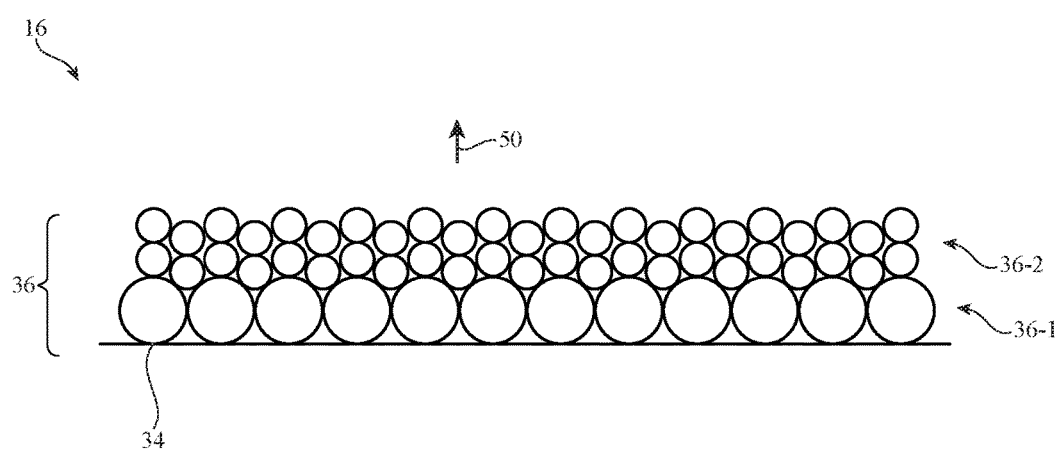
FIG. 7 is a cross-sectional side view of illustrative strap fabric with layers characterized by strands with different deniers per filament in accordance with an embodiment.

To enhance comfort, it may be desirable to incorporate moisture management structures within strap 16. For example, it may be desirable to incorporate fabric layers into strap 16 that promote the wicking of moisture away from the user's wrist. FIG. 7 is a cross-sectional side view of a portion of strap 16 in an illustrative configuration in which strap 16 contains fabric 36 having portions such as inner portion 36-1 (i.e., a layer facing wrist 34) and outer portion 36-2 (i.e., a layer facing the air above strap 16). Inner portion 36-1 may have strands of material with a larger linear density per filament (e.g., a larger denier per filament value) than outer portion 36-2. The smaller denier per filament value of layer 36-2 ensures that layer 36-2 has more surface area than layer 36-1 and therefore helps layer 36-2 create a strong capillary action that draws moisture outwardly through fabric 36 in direction 50. The smaller denier per filament value of layer 36-2 also promotes evaporation of moisture into the surrounding environment. The larger denier per filament of layer 36-1 allows rapid moisture movement from wrist 34 through fabric 36 in direction 50 and helps reduce moisture retention in fabric 36 near wrist 34 to enhance comfort. Portions of fabric 36 that contact wrist 34 may be modified to enhance comfort (e.g., strands of material in fabric layer 36-1 or other portions of fabric 36 in contact with wrist 34 may be bulked, air twisted, or brushed to enhance comfort).

Any suitable materials may be used in forming the strands of fabric 36. For example, the strands of material in fabric 36 may be formed from materials such as polyester, nylon (e.g., polyamide, nylon 6, nylon 6,6, etc.), or polypropylene. These materials may exhibit low moisture regain (low moisture absorbed into the bulk material of the strand), thereby preventing strap 16 from becoming saturated with moisture when a user's wrist becomes moist and helping to ensure that moisture is free to move through open pores in fabric 36 by capillary action.

Fabric 36 may include stands with any suitable filament count ranging from single filament strands (monofilaments) to strands with 50 or more filaments. The strands (yarns) may have any suitable denier per strand value and any suitable denier per filament value.

For example, weft strands for fabric 36 may be formed from 50 denier blended yarn having two intertwined strands each of which contains 53 filaments. If desired, the weft strands may have denier values of more than 25 denier per strand, more than 50 denier per strand, less than 100 denier per strand, less than 75 denier per strand, or other suitable values. Weft strands may have more than 20 filaments per strand, more than 40 filaments per strand, more than 100 filaments per strand, fewer than 150 filaments per strand, fewer than 120 filaments per strand, fewer than 70 filaments per strand, etc.

Fabric 36 for strap 16 may have warp strands with that each have a denier value of 50-150 denier, more than 40 denier, or less than 200 denier. The warp strands for moisture management layers such as layers 36-1 and 36-2 of FIG. 7 may each have 10-36 filaments, 2-150 filaments, more than 10 filaments, more than 20 filaments, more than 30 filaments, 10-13 filaments, 10-36 filaments, fewer than 36 filaments, 106 filaments, 30-120 filaments, fewer than 130 filaments, or other suitable number of filaments.

Loops in region 28L may be formed from warp strands having a denier of 150-250 and having 10-36 filaments, strands having a denier per filament of 10-20, 15, more than 10, or less than 20. If desired, these warp strands may have a denier of less than 300 or more than 100, or other suitable denier value and may have more than five filaments, fewer than 40 filaments, or other suitable number of filaments per strand.

Layer 36-1 may have a denier per filament of 3 and layer 36-2 may have a denier per filament of 1 (i.e., the ratio of the denier per filament values of layer 36-1 to 36-2 may be 3:1) or these layers may have other denier per filament values. For example, the denier per filament of layer 36-2 may be 1-6, may be more than 1, more than 2, more than 3, more than 5 less than 10, etc. The denier per filament of layer 36-2 may be 0.5-4, may be more than 0.5, more than 1, more than 2, more than 3, more than 5 less than 6, etc. The ratio of the denier per filament value of layer 36-1 to that of layer 36-2 may be 3, 2-4, more than 1.2, more than 1.5, more than 2, more than 3, more than 4, more than 8, less than 10, less than 5, or other suitable value.

Figure 8:
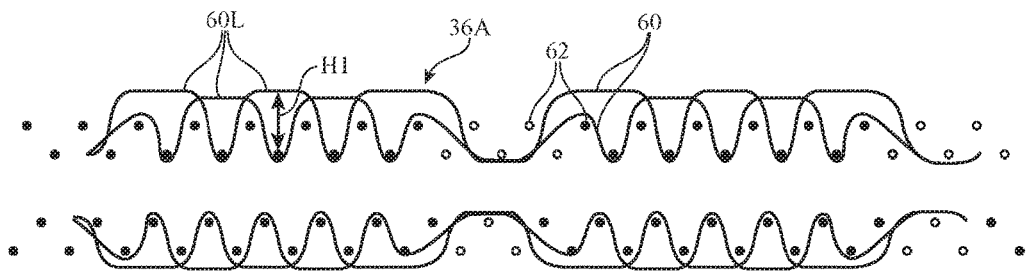
FIGS. 8, 9, and 10 are cross-sectional side views of portions of a fabric strap in accordance with an embodiment.
Figure 9:
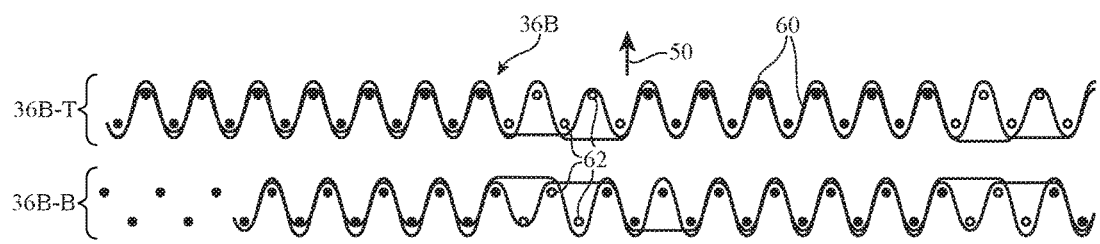
Figure 10:
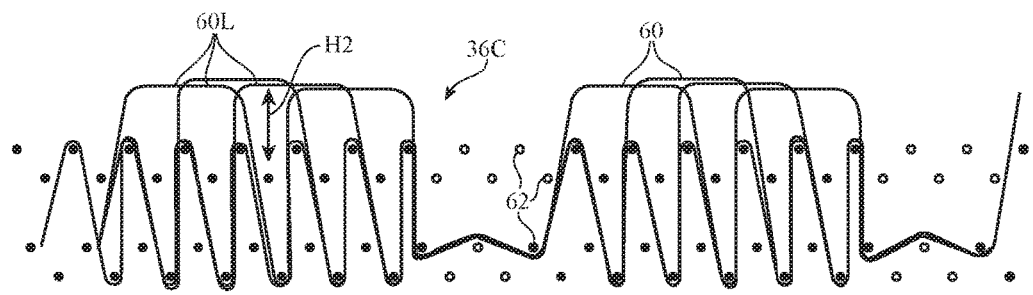
Figure 11:
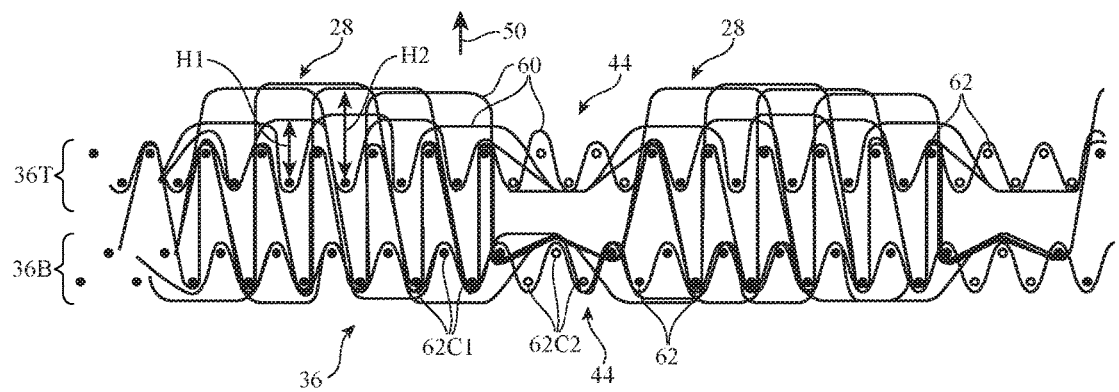
FIG. 11 is a cross-sectional side view of an illustrative fabric strap formed from the fabric structures of FIGS. 8, 9, and 10 in accordance with an embodiment.

FIGS. 8, 9, and 10 are cross-sectional side views of illustrative portions 36A, 36B, and 36C respectively of illustrative fabric layer 36 of FIG. 11. Fabric 36 of FIG. 11 may be a two-layer fabric, a four-layer woven fabric layer, a fabric formed from more than two layers, more than three layers, two to four layers, fewer than five layers, or other suitable number of layers. Fabric 36 of FIG. 11 may include warp strands 60 and weft strands 62.

Fabric 36 of FIG. 11 includes uppermost fabric layer 36T and lowermost fabric layer 36B. In this type of configuration, layer 36T (e.g., warp strands in layer 36T) may have a smaller denier per filament than layer 36B (e.g., warp strands in layer 36B) to promote moisture flow in direction 50.

If desired, two optional intermediate moisture management layers such as fabric layers 36-1 and 36-2 of FIG. 7 may be interposed between layers 36T and 36B. In this type of arrangement, fabric 36 may have four layers: 36B, 36-1, 36-2, and 36T. To promote moisture flow in direction 50, layer 36T (e.g., the warp strands in layer 36T) may have a denier per filament value that is less than (or is equal to) that of layer 36-2. Layer 36-2 (e.g., the warp strands in layer 36-2) may have a denier per filament value that is less than (or is equal to) that of layer 36-1. Layer 36-1 may have a denier per filament value that is less than (or is equal to) that of layer 36-B.

Fabric portion 36B of FIG. 9 may have upper layer 36B-T and lower layer 36B-B. To enhance moisture flow in direction 50, layer 36B-T may have a lower denier per filament value than layer 36B-B. In a two-layer fabric construction for fabric 36, layers 36B-T and 36B-B may have the properties of layers 36-2 and 36-1 of FIG. 7, respectively. In a four layer construction in which layers 36-2 and 36-1 are sandwiched between layers 36B-T and 36B-B, all four layers may have different denier per filament values to promote moisture flow.

As shown in FIG. 8, portion 36A of fabric 36 may have loop portions 60L in warp strands 60 that are characterized by loop size (height) H1. As shown in FIG. 10, portion 36C of fabric 36 may have loop portions 60L' in warp strands 60 that are characterized by larger loop size (height) H2. When portions 36A and 36C are woven together with portion 36B (and optionally with additional intermediate moisture management layers) to form fabric 36 of FIG. 11, the presence of multiple loop sizes such as loop sizes H1 and H2 on upper surface 28 of fabric 36 helps form effective fabric loops for loop portion 28L of strap 16 of FIG. 3. This ensures that hooks 32 will satisfactorily engage with the loops in portion 28L when strap 16 is placed in its closed (clasped) position.

If desired, loops and grooves may be formed on both outwardly facing and inwardly facing surfaces of strap 16 to provide strap 16 with a uniform appearance.

Stretchable warp strands may be interwoven with weft fibers 62 as described in connection with stretchable warp strands 40 of FIGS. 5A and 5B. Weft strands in grooves 44 such as weft strands 62C2 of FIG. 11 may have a different visual appearance (e.g., a different color) than weft strands that are not in grooves 44 such as weft strands 62C1), thereby allowing strands 62C2 to become increasingly visible to a user as strap 16 is stretched.

Although sometimes described in the context of straps and electronic devices with straps such as wristwatches, fitness bands, or other electronic devices, the features of strap 16 may be used in other contexts. For example, the fabric and other structures of strap 16 such as the strand loops and other structures used to form hook-and-loop fasteners, the strands of different denier per filament values that promote moisture wicking, the strands of stretchable material that allow the fabric to stretch, the grooves with differently colored strands that can be observed when the stretchable strands are stretched, and other features may, if desired be incorporated into other suitable fabric-based items, clothing items, enclosures (e.g., bags, backpacks, etc.). As examples, the features of strap 16 may be incorporated into clothing, straps for backpacks and other bags, belts, suspenders, straps for clothing, shirts, pants, coats, sweatshirts, sweaters, socks, hats, sidewalls and other structures in enclosures such as handbags, satchels, purses, etc., straps and other portions of purses, wallets, covers for electronic devices (e.g., sleeves for tablet computers, cellular telephones, laptop computers, etc.), or any other suitable items having intertwined strands of material.

The foregoing is merely illustrative and various modifications can be made to the described embodiments. The foregoing embodiments may be implemented individually or in any combination.

What is claimed is:

1. An electronic device, comprising:
a housing;
electrical components in the housing; and
a strap coupled to the housing, wherein the strap contains at least first and second fabric layers, wherein the first fabric layer has warp strands with a first denier per filament value, wherein the second fabric layer has warp strands with a second denier per filament value that is less than the first denier per filament value, wherein the first and second fabric layers have grooves that span the strap, wherein the first and second layers of the strap contain weft strands, and wherein a first set of the weft strands that is in the grooves has a different color than a second set of the weft strands that is not in the grooves.

2. The electronic device defined in claim 1 wherein the strap is configured to wrap around a body part of a user so that the first fabric layer faces the body part and so that the second fabric layer faces away from the body part.

3. The electronic device defined in claim 2 further comprising a hook-and-loop fastener formed from hooks at an end of the strap that are configured to engage loops at another end of the strap.

4. The electronic device defined in claim 3 wherein a portion of the warp strands in the second fabric layer forms the loops.

5. The electronic device defined in claim 4 wherein the portion of the warp strands that forms the loops includes a first set of warp strands that form loops of a first size and a second set of warp strands that forms loops of a second size that is different than the first size.

6. The electronic device defined in claim 1 wherein at least some of the warp strands are stretchable and wherein the first set of weft strands in the grooves is configured to become increasingly visible as the stretchable warp strands are stretched.

7. The electronic device defined in claim 6 wherein the housing comprises a watch housing and wherein the electrical components include a display mounted in the watch housing.

8. The electronic device defined in claim 1 wherein the strap comprises third and fourth fabric layers between the first and second fabric layers.

9. The electronic device defined in claim 8 wherein the third fabric layer is interposed between the first and fourth fabric layers, wherein the third and fourth fabric layers have warp strands, and wherein the warp strands of the third fabric layer have a smaller denier per filament value than the first denier per filament value.

10. The electronic device defined in claim 9, wherein the warp strands of the fourth fabric layer have a smaller denier per filament value than the warp strands of the third fabric layer.

11. The electronic device defined in claim 10 wherein the warp strands of the fourth fabric layer have a larger denier per filament value than the second denier per filament value.

12. An electronic device strap, comprising:
an inner fabric layer having warp strands with a first denier per filament value;
an outer fabric layer having warp strands with a second denier per filament value that is less than the first denier per filament value; and
a hook-and-loop fastener formed from hooks coupled to the inner fabric layer and loops formed from portions of the warp strands in the outer fabric layer wherein the loops include loops of a first size formed from a first set of warp strands in the outer fabric layer and include loops of a second size formed from a second set of warp strands in the outer fabric layer and wherein the first and second sizes are different.

13. The electronic device strap defined in claim 12 further comprising third and fourth fabric layers interposed between the inner and outer fabric layers.

14. The electronic device strap defined in claim 12 wherein at least some of the warp strands are formed from stretchable polymer.

15. An electronic device, comprising:
a housing;
a display mounted in the housing; and
a strap having portions coupled to opposing sides of the housing, wherein the strap includes a hook-and-loop fastener having hooks on an inner fabric layer of the strap and having loops formed from strands of material in an outer fabric layer of the strap, wherein the inner and outer fabric layers have warp strands, weft strands, and grooves, wherein a first set of the weft strands is in the grooves and a second set of the weft strands is not in the grooves, wherein at least some of the warp strands are stretchable, and wherein the first set of the weft strands in the grooves become increasingly visible as the stretchable warp strands are stretched.

16. The electronic device defined in claim 15 wherein the outer fabric layer comprises:
a first set of warp strands that form loops of a first size; and
a second set of warp strands that form loops of a second size that is different than the first size, wherein the inner fabric layer has warp strands with a first denier per filament value and wherein the outer fabric layer has warp strands with a second denier per filament value, and wherein a ratio of more than two is formed by dividing the first denier per filament value by the second denier per filament value.

17. The electronic device defined in claim 15 wherein the first set of the weft strands that is in the grooves has a different color than the second set of the weft strands that is not in the grooves.

* * * * *